United States Patent [19]

Schroeder et al.

[11] 4,165,324
[45] Aug. 21, 1979

[54] REMOVAL OF PHTHALIDE FROM IMPURE PHTHALIC ANHYDRIDE

[75] Inventors: Hobe Schroeder, Warrenville; Stanley J. Kulpa, Chicago, both of Ill.

[73] Assignee: Standard Oil Company (Indiana), Chicago, Ill.

[21] Appl. No.: 898,930

[22] Filed: Apr. 24, 1978

[51] Int. Cl.² .............................................. C07D 307/89
[52] U.S. Cl. ................................................. 260/346.7
[58] Field of Search ...................................... 260/346.7

[56] References Cited

U.S. PATENT DOCUMENTS

| 1,817,304 | 8/1931 | Foster | 260/346.7 |
| 2,670,325 | 2/1954 | West et al. | 260/346.7 |
| 3,155,688 | 11/1964 | Tomlinson | 260/346.7 |

Primary Examiner—John M. Ford
Assistant Examiner—Bernard Dentz
Attorney, Agent, or Firm—Fred R. Ahlers; Arthur G. Gilkes; William T. McClain

[57] ABSTRACT

Phthalide, one intermediate in the oxidation of o-xylene to phthalic acid or its anhydride, is unique in that it is the only intermediate oxidation product which cannot be economically removed from said anhydride by fractional distillation or crystallization. According to the present invention, impure phthalic anhydride containing phthalide is heated to a temperature of at least 200° C. in the presence of a catalytic amount of an alkali metal hydroxide having a molecular weight above 40. By such heat treatment of impure phthalic anhydride its phthalide content can be decreased to at least 0.1 weight percent and even to below the analytically detectable concentration of 0.001 weight percent (10 ppm by weight).

3 Claims, No Drawings

REMOVAL OF PHTHALIDE FROM IMPURE PHTHALIC ANHYDRIDE

PRIOR ART BACKGROUND

The commercial preparation of phthalic acid anhydride (PAN) was accomplished first by the oxidation of naphthalene or o-xylene with chemical oxidants, then about 70 years ago the vapor phase oxidation of naphthalene and about 30 years ago by the vapor phase oxidation of o-xylene low in m- and p-xylene isomers. Both vapor phase oxidations use rather large volumes of air and solid particulate catalyst containing vanadium pentoxide. The general route devised for the recovery of commercially acceptable PAN product from the impure PAN produced by such vapor phase oxidation of naphthalene included the step of heating such impure PAN as a liquid, e.g., at a temperature in the range of from 130° C. up to 285° C., for up to 24 to 48 hours prior to a two step distillation sequence comprising simple total distillation followed by fractional distillation. The heating step converted oxidation coproducts which were color bodies or color formers into condensation products boiling at a temperature well above the boiling temperature of PAN. Hence such heat treating step was devised mainly to solve a product color problem but also to overcome product discoloration upon aging. It was found that the duration of the heat treating step could be substantially reduced by the use of chemical agents which promoted the condensation reactions. According to U.S. Pat. No. 3,407,216, impure PAN from vapor phase oxidation of naphthalene does not contain phthalide as an impurity.

After the use of o-xylene feeds containing not more than 15 percent m- and p-isomers had been demonstrated as a feasible feed for the vapor phase air oxidation to produce impure PAN, its purification used the established combination of heat treating followed by simple distillation and fractional distillation.

The time shortening color removal heat treating for impure PAN frm naphthalene or o-xylene feeds was suggested as being accomplished through the use of lithium and/or sodium nitrates (U.S. Pat. No. 2,512,283); carbonates, bicarbonates, sulfates or borates (U.S. Pat. No. 2,671,054); or phthalates added per se or formed in situ from the alkali metal hydroxides (U.S. Pat. No. 2,670,325). U.S. Pat. No. 3,155,688 specifically claims the use of potassium hydroxide and its salts with acids weaker than phthalic acid, as additive for color removal during heat treatment of impure PAN obtained by vapor phase oxidation of naphthalene. U.S. Pat. No. 2,670,325 specifically discloses the use of 0.05 weight percent sodium hydroxide as additive for color removing heat treatment of the impure PAN products obtained by vapor phase oxidation of naphthalene and o-xylene.

With respect to the removal of phthalide from PAN, we have reviewed the techniques for such removal as were brought to our attention by search reports resulting from searching conducted in Volumes 1 to 85 (1907 through 1976) of Chemical Abstracts, Derwent's Patent and Literature Abstracts (1964–1976) as well as pertinent information retrieved by machine search of the patents abstracted and indexed by Information For Industry of United States Patents granted from 1950 through 1975. We noted that the use of alkali metal hydroxides according to the technique of U.S. Pat. No. 2,670,325 was not there nor in any other publication found recognized as an agent useful for removing phthalide from impure PAN. We also noted that since phthalide is an intermediate incomplete oxidation product of o-xylene in the route to phthalic acid and/or phthalic anhydride, it is not surprising that the techniques previously proposed for removing phthalide from PAN involve the oxidation of phthalide.

Air or oxygen gas has been used to complete the oxidation of phthalide, preferably in the presence of a catalyst. Vanadium pentoxide catalyst is used in the heat treatment step or in the subsequent fractionation step in either the liquid or vapor phase according to Published German Patent Application (OLS) No. 1,935,008. The phthalide oxidation technique of French Pat. No. 1,600.064 involves the use of chromium, cobalt or vanadium with the impure PAN in an autoclave pressurized with oxygen or air to decrease the phthalide concentration to less than 0.1 weight percent. Liquid phase air oxidation of phthalide in impure PAN in the presence of cobalt, manganese and bromine is the phthalide removal technique taught by U.S. Pat. No. 3,208,423.

However, chemical oxidative removal of phthalide during the step of heat treating impure and discolored PAN has been an equally proposed technique. The use of sulfuric acid as oxidant in a particular mixture of phthalide, phthalic acid and phthalic anhydride is disclosed by U.S. Pat. No. 3,407,216. Japanese Published Patent Publication No. 10333/70 teaches the use during the heat treatment of impure PAN of potassium salts of different sulfur-containing acids; e.g., $KHSO_3$, $K_2S_2O_5$, $KHS_2O_4$, $K_2S_2O_4$, and $K_2SO_3$. German Published Patent Application (OLS) No. 2,417,145 suggests adding a mixture of sodium carbonate and sodium nitrate to the impure PAN charged to the heat treating step. U.S. Pat. No. 3,338,924 discloses using a peroxide in combination with an alkali metal hydroxide and/or alkali metal carbonate during the heating treating of impure PAN to oxidize phthalide.

SUMMARY OF THE INVENTION

We have discovered that phthalide can be successfully decreased down to a concentration of at least 0.1 weight percent by the use of a catalytic amount; e.g., from 1 to 10 milligram moles per gram mole of impure phthalic anhydride, of an alkali metal hydroxide of molecular weight of at least 40 (e.g., M.W. of 40, 56, 102 or 150) during the heat treatment of impure PAN provided the heat treatment is conducted with impure PAN in the liquid phase at a temperature above 200° C., e.g., in the range of from 250° C. up to 350° C., and preferably within the range of from 275° C. up to 300° C. The hydroxides of rubidium and cesium at present cost are several hundred times the cost of sodium and potassium hydroxides and hence are not preferred for use in the present inventive phthalide removal method.

For use of the preferred sodium and potassium hydroxide additives, the heat treating temperature should be at least 250° and preferably should be at least the normal boiling (760 mm Hg) temperature, about 275° C., of the impure PAN. For example, the reaction rate constant (K min.$^{-1}$) calculated from the slopes of the straight portion of the curves (plotted on semilogarithmic paper) of phthalide against time are $6.7 \times 10^{-3}$ min.$^{-1}$ at 250° C. and $6.9 \times 10^{-2}$ min.$^{-1}$ at 275° C. at the same concentration 3.7 milligram mole of KOH per gram mole of impure PAN. Expressed differently, the half period of phthalide (time for phthalide concentration to diminish by one-half) in the heat treating step in the presence of such concentration of KOH is about 103 minutes at a temperature of 250° C. but only 10 minutes at 275° C., and, by extrapolation, is more than two weeks at 200° C.

The following data in TABLE I illustrate the effectiveness of different alkali metal hydroxides used at 3.7 milligram moles per gram mole of impure PAN. Samples of the same impure (0.78 wt.% phthalide) PAN were used for each heat treating step conducted at a temperature of 275° C. for four hours. After such heat treating step the impure PAN samples were analyzed for their phthalide content.

TABLE I

| Additive | Residual Phthalide, Wt. % |
| --- | --- |
| LiOH | 0.37 |
| NaOH | 0.21 |
| KOH | 0.008 |
| RbOH | 0.007 |
| CsOH | <0.001* |

*Limit of analytical detection is 10 ppm by weight.

It was indeed surprising to find a substantial break in effectiveness of the alkali metal hydroxides to exist as indicated above, rather than a gradual change in effectiveness in the direction of the known increase in basicity of the hydroxides. It is even more surprising that such substantial break in effectiveness came between sodium and potassium hydroxides. Because of such substantial break, potassium hydroxide is the most preferred alkali metal hydroxide for the present invention.

The effect of temperature on phthalide removal during the heat treating step can be shown by the following results of samples of the same impure PAN containing the same concentration of phthalide heated in the presence (0.14 wt.%) or absence of KOH to temperatures of 200°, 250° and 275° C. for four hours, fractionated at 100 mm Hg pressure in a 20 tray Oldershaw column and the PAN distillates were then analyzed for their phthalide content.

TABLE II

4 HOUR HEAT TREATMENT TO REMOVE PHTHALIDE

| | Phthalide Concentration, wt.% | |
| --- | --- | --- |
| Temperature, °C. | No KOH | 0.14 wt.% KOH |
| 200 | 1.32 | 1.05 |
| 250 | 1.10 | 0.16 |
| 275 | 1.68 | <0.001 |

It will be noted that heating impure PAN at 200° C. in the presence of KOH was not significantly better than heating in the absence of KOH. Also, it will be noted that merely increasing the temperature (i.e., no KOH) of the heat treating step does not per se cause a marked decrease in phthalide content.

The rate of decrease of phthalide removal at temperatures of 250° C. and 275° C. are shown by the following experimental data obtained from two solid samples of impure PAN initially containing 2.0 weight percent phthalide to each of which was added 0.14 wt.% KOH (3.7 milligram mole KOH per gram mole PAN). One such sample was heated at 250° C. and its phthalide content, as determined by analysis, is the 0 time composition of 1.82 weight percent phthalide shown below in the 250° C. column. The other such sample was heated to 275° C. and its phthalide content, as determined by analysis, is the 0 time composition of 1.37 weight percent shown below in the 275° C. column.

TABLE III

| Time, | Phthalide Content, wt. % at | |
| --- | --- | --- |
| hour | 250° C. | 275° C. |
| 0 | 1.82 | 1.37 |
| 0.25 | 1.54 | 0.52 |
| 0.50 | 1.45 | 0.16 |
| 1 | 1.42 | 0.021 |
| 2 | 0.96 | 0.002 |
| 4 | 0.45 | <0.001 |
| 6 | 0.16 | <0.001 |

A comparison of the present inventive phthalide removal technique with some of the prior art chemical oxidative removal techniques are shown in TABLE IV below. The chemical oxidants were used in amounts equimolar with phthalide in the impure PAN heat treating step conducted for four hours at the reflux temperature of boiling impure PAN.

TABLE IV

| Additive | Residual Phthalide Content, wt.% |
| --- | --- |
| $NaBO_2$ | 1.16 |
| $KHSO_5$ | 1.14 |
| $H_2O_2$ (30% solution) | 0.88 |
| $Na_2CO_3$ | 0.83 |
| $NaNO_3$ | 0.21 |
| $NaNO_3$ & $NaCO_3$ | 0.81 |
| KOH (0.3 wt.%) | <0.001 |

The impure PAN having 1.82 weight percent phthalide at 0 time when heated in the presence of 0.14 weight percent KOH at the 275° C. (reflux) temperature of boiling impure PAN at atmospheric pressure for four hours was found to have no detectable, i.e., less than 0.001 weight percent, phthalide.

Each of the five PAN compositions shown below were heated to reflux temperature (275° C.) for four hours and then analyzed for its phthalide content except for Composition 5 which after the four hour heating at 275° C. was distilled at 100 mm Hg in a 20 tray Oldershaw column and the PAN distillate was analyzed for its phthalide content. The weight percent of each of the components shown is based on the PAN.

TABLE V

| Composition | Initial Phthalide, Wt. % | 2-CBA* Wt. % | KOH Wt. % | Final Phthalide, Wt. % |
| --- | --- | --- | --- | --- |
| 1 | 1 wt.% | 0 | 0 | 0.78 |
| 2 | 1 wt.% | 0 | 0.26 | <0.001 |
| 3 | 1 wt.% | 1 | 0 | 0.62 |
| 4 | 1 wt.% | 1 | 0.26 | <0.001 |
| 5 | 0.78 wt.% | | 0.14 | <0.001 |

*2-CBA is 2-carboxybenzaldehyde.

Further comparison of the effectiveness of sodium and potassium hydroxides as a phthalide removal agent in the heating step are shown in TABLE VI below. The data shown were obtained by using said hydroxides in the concentrations shown with PAN initially containing one weight percent phthalide. Each composition was heated for four hours at its reflux (275° C.) temperature and then analyzed for its final phthalide content.

TABLE VI

| Composition | Agent, wt. % | | Final Phthalide, wt. % |
| --- | --- | --- | --- |
| 1 | NaOH, | 0.1 | 0.17 |
| 2 | NaOH, | 0.15 | 0.11 |
| 3 | KOH, | 0.09 | <0.001 |

TABLE VI-continued

| Composition | Agent, wt. % | Final Phthalide, wt. % |
|---|---|---|
| 4 | KOH, 0.14 | <0.001 |

The TABLE VI weight percent amounts of sodium and potassium hydroxide correspond to ratios of 3.7 and 5.5 milligram moles of sodium hydroxide and 2.4 and 3.7 milligram moles of potassium hydroxide per gram mole of PAN. On such ratio basis, the sharp differences in effectiveness for decreasing phthalide concentration during the heat treating step favors the use of potassium hydroxide over sodium hydroxide. At the concentration of 3.7 milligram mole per gram mole of PAN, sodium hydroxide could not, as did potassium hydroxide, decrease the phthalide concentration to less than 10 ppm. Even increasing the use of sodium hydroxide by 50% from 3.7 to 5.5 milligram moles per gram mole of PAN did not decrease the phthalide concentration to 10 ppm. The final phthalide concentration was still more than 10 ppm. However, in spite of the decrease in the use of potassium hydroxide from 3.7 to 2.4 milligram moles KOH per gram mole of PAN, the decrease in phthalide concentration was again to less than 10 ppm.

We have disclosed, described and illustrated the present inventive method for decreasing the phthalide content of impure PAN for the understanding of those skilled in the art so that such persons would be able to practice the inventive method and obtain its benefits. Such persons can, it is submitted, readily operate at conditions outside those above illustrated by making readily perceivable changes but without undue experimentation and still be within the spirit and scope of the invention hereafter claimed.

The invention claimed is:

1. A method of decreasing the phthalide content of impure phthalic anhydride during its heat treatment in the liquid phase which comprises conducting said heat treatment at a temperature upward from 250° C. in the presence of a catalytic amount of an alkali metal hydroxide selected from the group consisting of potassium hydroxide, rubidium hydroxide or cesium hydroxide.

2. The method of claim 1 wherein the alkali metal hydroxide is potassium hydroxide, the heat treatment is conducted at a temperature of at least 250° C. and the catalytic amount of KOH is in the range of from 1 to 10 milligram-moles per gram mole of phthalic anhydride.

3. The method of claim 2 wherein the heat treatment is conducted in the presence of from 0.1 to 0.3 weight percent KOH based on impure phthalic anhydride and at a temperature from 260° C. up to the boiling temperature of impure phthalic anhydride.

* * * * *

UNITED STATES PATENT OFFICE
CERTIFICATE OF CORRECTION

Patent No. 4,165,324      Dated August 21, 1979

Inventor(s) Hobe Schroeder and Stanley J. Kulpa

It is certified that error appears in the above-identified patent and that said Letters Patent are hereby corrected as shown below:

| Col. | Line | | | | |
|---|---|---|---|---|---|
| 1 | 41 | reads | "frm" | should read | --from-- |
| 2 | 15 | " | "1,600.064" | " | --1,600,064-- |
| 2 | 38 | " | "heating treating" | " | --heat treating-- |
| 2 | 59 | " | "250°" | " | --250°C-- |
| 2 | 65 | " | "min.$^{-1}$ 1" | " | --min.$^{-1}$-- |

Signed and Sealed this

Eighteenth Day of December 1979

[SEAL]

Attest:

SIDNEY A. DIAMOND

Attesting Officer     Commissioner of Patents and Trademarks